(12) United States Patent
Marobbio et al.

(10) Patent No.: US 8,716,250 B2
(45) Date of Patent: May 6, 2014

(54) DIAZOXIDE FOR THE TREATMENT OF FRIEDREICH'S ATAXIA

(75) Inventors: Carlo Marya Thomas Marobbio, Bari (IT); Luigi Palmeri, Bari (IT); Ferdinando Palmeri, Bari (IT); Antonella Santoro, Bari (IT)

(73) Assignee: Universita' Degli Studi di Bari (IT)

( * ) Notice: Subject to any disclaimer, the term of this patent is extended or adjusted under 35 U.S.C. 154(b) by 50 days.

(21) Appl. No.: 12/511,460

(22) Filed: Jul. 29, 2009

(65) Prior Publication Data
US 2010/0029576 A1 Feb. 4, 2010

(30) Foreign Application Priority Data

Jul. 30, 2008 (IT) .............................. MI2008A1409

(51) Int. Cl.
| | | |
|---|---|---|
| *A01N 43/04* | (2006.01) | |
| *A61K 31/70* | (2006.01) | |
| *C07C 205/00* | (2006.01) | |
| *C07C 207/00* | (2006.01) | |
| *C07C 229/00* | (2006.01) | |
| *C07D 285/16* | (2006.01) | |

(52) U.S. Cl.
USPC .................. 514/23; 562/553; 562/575; 544/7

(58) Field of Classification Search
CPC ............................ A61K 31/198; A61K 31/549
USPC ........................... 514/23; 562/553, 575; 544/7
See application file for complete search history.

(56) References Cited

U.S. PATENT DOCUMENTS

2004/0241256 A1* 12/2004 Ehrenpreis et al. ............ 424/734
2005/0202394 A1* 9/2005 Dobson .......................... 435/1.1

FOREIGN PATENT DOCUMENTS

WO 2008/064296 A 5/2008

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
Delatycki, M.B., Williamson, R., Forrest, S.M. (2000) Friedreich ataxia: an overview. Journal of Medical Genetics, vol. 37, p. 1-8.*
"Cardiomyopathy" from the National Hearth Lung and Blood Institute, National Institutes of Health, U.S. Department of Health & Human Services [online], [retrieved May 31, 2011]. Retrieved from the internet <http://www.nhlbi.nih.gov/health/dci/Diseases/cm/cm_all.html>.*
"Scoliosis" from the Merck Manual Home Edition [online], [retrieved May 31, 2011]. Retrieved from the internet <http://www.merckmanuals.com/home/print/sec23/ch278/ch278b.html>.*
Basabe, J.C., Lopez, N.L., Viktora, J.K., Wolff, F.W. (1971) Insulin Secretion Studied in the perfused Rat Pancreas. I. Effect of Tolbutamide, Leucine and Arginine; Their Interaction with Diazoxide, and Relation to Glucose. Diabetes, vol. 20, p. 449-456.*
Voncken Max et al: "Friedreich ataxia: Update on pathogenesis and possible therapies" Neurogenetics, Oxford University Press, Oxford, GB vol. 5, No. 1, Feb. 1, 2004, pp. 1-8.
Herbert M D et al: "Gene-based approaches toward Friedreich ataxia therapeutics" Cellular and Molecular Life Sciences, vol. 64, No. 23, Dec. 2007, pp. 3034-3043.

* cited by examiner

*Primary Examiner* — Scarlett Goon
(74) *Attorney, Agent, or Firm* — Hess Patent Law Firm LLC; Robert J. Hess

(57) ABSTRACT

A pharmaceutical preparation treats Friedreich's ataxia and treats or prevents pathologies related thereto. In particular, the pharaceutical preparation concerns the use of diazoxide or 7-chloro-3-methyl-4H-1,2,4 benzothiadiazine 1,1-dioxide, in combination with glucose and/or leucine, for the treatment of Friedreich's ataxia (FRDA) and for the treatment or prevention of pathologies related thereto.

6 Claims, 11 Drawing Sheets

D = diazoxide
G = glucose
L = leucines
CTR = control

Figure 5: Western Blot

Figure 6: Western Blot

DIAZOXIDE FOR THE TREATMENT OF FRIEDREICH'S ATAXIA

BACKGROUND OF THE INVENTION

The present invention concerns a pharmaceutical preparation for the treatment of Friedreich's ataxia and for the treatment or prevention of pathologies related thereto.

The term ataxia is used in medicine to identify a lack of motor coordination. In fact, a person affected by ataxia loses his/her harmony of movement. Said term also refers to a group of rare, progressive and seriously invalidating diseases of the central nervous system. Said pathologies can stem from inflammatory, infective, metabolic and tumoural causes, but the degenerative and hereditary forms are the most frequent. Of these, the most common form is Friedreich's ataxia (FRDA) which affects one in 50,000 people; it is the dominant autosomal-recessive form in terms of frequency.

The pathology is caused by expansion of the GAA triplet in the gene codifying for a protein called frataxin (chromosome 9q13). The most common gene mutation is the repetition of the GAA triplet located in the first intron of the gene. The sequence of these nucleotide bases, which usually has a maximum of 40 triplets in normal individuals, expands to a few hundred in patients affected by the pathology. The effect is a marked reduction in the RNA level of the frataxin and in the quantity of frataxin expressed, even though a very small quantity continues to be produced.

Frataxin is a mitochondrial protein involved in the homeostasis of iron inside the mitochondria. It has been observed that there is a correlation between the disease and the size of expansion of the GAA triplet. From the biological point of view, the quantity of frataxin produced is inversely proportional to the dimensions of the expansion. From the clinical point of view, the age at which the diseases occur depends on the residual quantity of normal protein produced.

Experimental studies on micro organisms, such as yeast, have shown that destruction of the frataxin gene causes:
  a marked increase in the concentration of iron in the mitochondria;
  an increase in sensitivity to oxidising factors;
  loss of the mitochondrial function, or a deficit in the cell respiratory function.

There is evidence that in the human disease there is increased oxidative stress and the two possible treatments, at the moment at least, are:
  removal of the excess iron from the mitochondria, an approach requiring suitable non-toxic drugs which are not yet available; and
  the use of anti-oxidant drugs which, although generally well tolerated, are nevertheless toxic for the organism, albeit at a low level.

The antioxidant drugs constitute a very broad and diverse family of medicaments and it could be extremely difficult to determine the most appropriate drug for this disease.

From the clinical point of view, FRDA usually occurs in infancy or adolescence, and less frequently in adults. Characterised by a progressive loss of motor coordination, the first symptoms are difficulty in running and in sports activities in general. The lower limbs are generally the first to be affected, causing instability during walking. Subsequently problems with coordination of the hands and with speech occur. Although the disorders are progressive, the course of the illness is variable. Many patients nevertheless become confined to a wheelchair.

Other common symptoms of FRDA are pes cavus, i.e. feet with very high arches, which usually does not require any particular treatment, and scoliosis, i.e. curvature of the spine, which must be kept under control as it can worsen during adolescence. Failing cure, symptomatic treatment must be provided aimed at preventing complications. It is essential to combat scoliosis in order to maintain the seated position and respiratory function.

90% of people affected by FRDA have heart problems, such as:
  increased cardiac frequency;
  thickening of the walls of the ventricular septum;
  electrocardiogram alterations (ECG).

It is therefore important for patients to have an electrocardiogram and an echocardiogram once a year. These alterations can be controlled, if necessary, by specific drugs such as ibedenone, which belongs to the category of the antioxidants. Although 85% of children treated with ibedenone presented an improvement in some of the symptoms, its benefits at neurological level were practically nil.

20% of patients develop diabetes mellitus and periodically checks on glycaemia in the blood are therefore recommended. This disorder can initially be controlled simply via a balanced diet or tablets. Diabetes can sometimes be the first symptom of FRDA.

Currently there is no evidence of an effective pharmacological therapy. Despite the numerous research studies carried out, no treatment is available at present to cure FRDA or slow down its progress.

A known pharmacological agent derived from benzothiazine is diazoxide or 7-chloro-3-methyl-4H-1,2,4 benzothiadiazine 1,1-dioxide. The molecule has the following structural formula

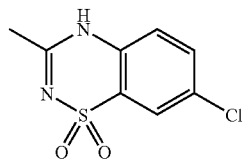

and is an activator of the $K^+$ channels, causing the opening of said channels.

In medical practice said pharmacological agent is used for example in the treatment of acute hypertension.

As an antihypertensive agent, diazoxide is administered intravenously and its effect has a very variable duration (from a few hours to several days). It performs a muscle relaxant action on the hypertensive arterioles by opening the potassium channels, resulting in hyperpolarisation of the cell membranes of the vasal smooth muscles. Diazoxide binds the plasmatic proteins and is eliminated partly via the kidneys after metabolization in the liver, but due to its non-optimal pharmacodynamic characteristics, it is used as an emergency drug.

SUMMARY OF THE INVENTION

The present invention concerns the use of diazoxide or 7-chloro-3-methyl-4H-1,2,4 benzothiadiazine 1,1-dioxide for the treatment of Friedreich's ataxia (FRDA) and for the treatment or prevention of related pathologies.

The object of the present invention is therefore the use of diazoxide for the treatment of Friedreich's ataxia (FRDA) and for the treatment or prevention of related pathologies.

A further object of the present invention is a pharmaceutical composition for use in the treatment of Friedreich's ataxia and for the treatment or prevention of related pathologies. A further object of the present invention is the use of diazoxide to induce expression of the frataxin gene and frataxin itself. A further object of the present invention is to provide a new drug useful for the treatment of FRDA.

Another object of the present invention is the use of diazoxide to combat the neurological effects of FRDA. An object of the invention is also a process for determining and/or evaluating the expression levels of the frataxin gene and frataxin itself.

Thus, according to another of its aspects, the invention also concerns a process for evaluating the expression levels of the frataxin gene and frataxin itself in cell samples.

According to yet another of its aspects, the invention also concerns a process for evaluating the expression levels of the frataxin gene and frataxin itself in a biological sample isolated from patients affected by FRDA.

With the present invention it is therefore possible to increase the frataxin expression level.

Optimisation of the frataxin expression according to the present invention is possible via the use of diazoxide in combination with glucose and/or leucine, in doses suitable for increasing the frataxin levels.

In fact, it has been seen that in FRDA patients, the expression level of the frataxin protein is very low; particularly, the more serious and invalidating the level of the pathology in progress, the lower the expression level of the frataxin protein.

Therefore low frataxin levels, in terms of quantity of frataxin being present in the cells and therefore in the organism of persons affected by FRDA, correlate in a directly proportional manner with a complex and particularly severe clinical situation. Surprisingly, the use of diazoxide in combination with glucose and/or leucine, according to the invention, raises the frataxin levels, thus obtaining a regression in the symptoms connected with Friedreich's ataxia disease.

Diazoxide is used in the known art for therapeutic indications different from those of the present invention and is furthermore associated with non-optimal pharmacokinetic characteristics limiting use thereof, despite its potential use. According to the present invention, on the other hand, said diazoxide is surprisingly advantageously used for the treatment of a "complex" pathology like FRDA and even more surprisingly its therapeutic potential is particularly effective due to the combination of said diazoxide with glucose and/or leucine.

The combination of diazoxide with glucose and/or leucine is therefore completely unexpected and able to achieve surprising results. Diazoxide, glucose and/or leucine in fact show a particularly surprising synergic effect when used in combination.

Proofs of the surprising synergic effect, due to the combination of said diazoxide with glucose and/or leucine, are provided by tests in vitro perfomed on samples of cells of patients affected by FRDA. The cells of patients affected by FRDA, in particular lymphoblastoid cell lines of patients, subsequently immortalized, were treated with different concentrations of diazoxide in combination with glucose and/or leucine.

DESCRIPTION OF THE PREFERRED EMBODIMENTS

Figure 1:
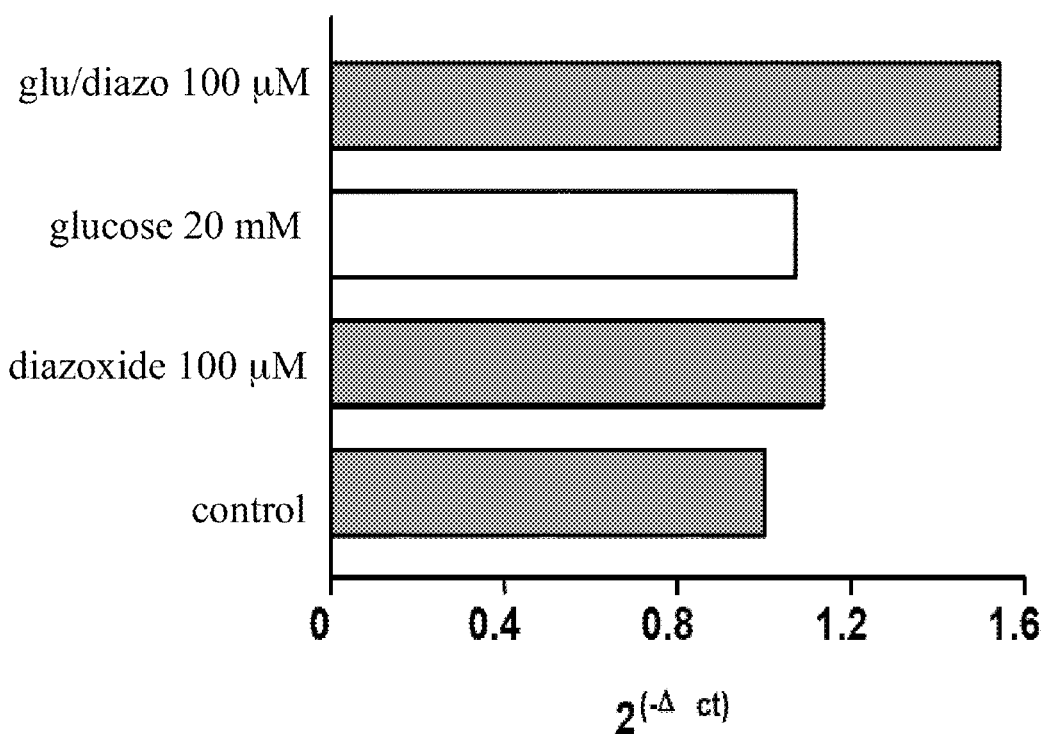
FIG. 1 a histogram showing results from cells treated with diazoxide 100 .mu.M with glucose 20 mM having an increased quantity of frataxin with respect to the non-treated control and with respect to the same cells treated alternatively with diazoxide or glucose.

According to a preferred aspect of the present invention, said concentrations of diazoxide are between 20 nM and 350 µM, preferably between 25 nM and 250 µM, and even more preferably between 25 µM and 100 µM.

Again according to a preferred aspect of the invention, the concentration of glucose is between 4 mM and 35 mM, preferably between 10 mM and 30 mM, even more preferably between 15 mM and 20 mM.

Again according to another preferred aspect of the invention, the concentration of leucine is between 4 mM and 20 mM, preferably between 7 mM and 15 mM, and even more preferably is equal to 10 mM.

According to a particularly preferred aspect of the present invention, the diazoxide is used at a concentration of 100 µM in combination with glucose 20 mM and/or leucine 10 mM.

The pharmaceutical preparations according to the present invention, which are used to increase the frataxin expression in FRDA patients, comprise diazoxide in combination with glucose and/or leucine, administered in any acceptable pharmaceutical form. The suitable forms can be single dosage forms, like tablets, capsules and similar, or injectable solutions (for example intravenous or intramuscular) or by infusion, or nasal sprays, nanoparticles or implants. The suitable pharmaceutical forms can also be freeze-dried products which can be administered, for example, by the intravenous, intramuscular, intracranial or intranasal route.

The invention also concerns the use of a pharmaceutical preparation which comprises diazoxide in combination with glucose and/or leucine, to increase the expression levels of the frataxin protein.

In the pharmaceutical compositions of the present invention for oral, subcutaneous, intravenous, transdermal or topical administration, the diazoxide, if necessary in a mixture with the other components, is preferably administered in one single dose, in a mixture with the traditional pharmaceutically acceptable excipients or carriers. The used dose can vary according to the age, weight and state of health of the patient, or according to the severity of the pathology and the chosen administration route.

According to one embodiment, the invention concerns a process for determining and/or evaluating the expression levels of the frataxin gene and frataxin itself which comprises:
a) treating a cell culture or a biological sample isolated from a patient affected by FRDA with diazoxide, if necessary in a mixture with glucose and/or leucine;
b) extracting and reverse-transcribing the total RNA;
c) amplifying and quantifying the frataxin transcripts;
d) analysing and processing the results.

Again according to the present invention, "cell culture" or "cell line" indicates a population of cells suitable for evaluating the expression levels of the frataxin gene and relative frataxin protein.

According to the present invention, "isolated biological sample" indicates a biological sample taken and isolated from an FRDA patient. According to the present invention, "sample" indicates a sample taken from the cell line treated with diazoxide, in combination with glucose and/or leucine. According to the present invention, "target" indicates the frataxin gene, transcript or protein.

According to a particularly preferred embodiment, the invention concerns a process for determining and/or evaluating the expression levels of the frataxin gene and protein which comprises:
a') treating a cell culture or a biological sample isolated from an FRDA patient with diazoxide, if necessary in a mixture with glucose and/or leucine;
b') extracting and reverse-transcribing the total RNA;
c') amplifying and quantifying the frataxin and control transcripts;
d') analysing and processing the results by evaluating amplification of the frataxin gene mRNA by means of ΔΔCt method corrected for efficiency of amplification of the target gene (frataxin) and the reference gene (actin).

In step (a') the cell line or the isolated biological sample are treated with diazoxide, preferably in the presence of glucose. In step (b') all the RNA present in the cells is extracted.

The extraction of the RNA can be performed according to the known techniques. Some details of preferred embodiments of the invention are nevertheless provided in the experimental section of the present description.

By way of example, the extraction can be performed using the QIAconnect Gene Expression Kit (Qiagen) or according to other known methods suitable for said operation and the relative dosage can be performed using spectrophotometric instruments known to a person skilled in the art.

After reverse-transcription of the RNA extracted, advantageously performed, for example, with GeneAmp RNA PCR core kit (Applied Biosystems), the amplification and qualification of step (c') can be performed according to the techniques known to a person skilled in the art, for example according to Real Time RT-PCR technology.

With said technology, in fact, it is possible to follow in real time the amplification phases, during the exponential phase, and simultaneously quantify the amplificate by evaluation of the fluorescence value emitted.

According to a preferred embodiment of the present invention, quantification of the reverse-transcribed product is carried out using fluorescent probes capable of hybridizing (and therefore specifically pairing) regions of the DNA of interest. By way of example and according to an advantageous embodiment of the invention, the probes used are Probe Hs 00175940_m1 and Probe Hs 99999903_m1 (Applied Biosystems). Particularly the probe defined Hs 00175940_m1 represents the specific probe capable of recognising and hybridizing the human frataxin gene, while the probe Hs 99999903_m1 recognises the human actin and represents the reference gene for normalisation of the values obtained.

The expression "threshold cycle" indicates the amplification reaction cycle, specific for each sample, in which the fluorescence signal of the sample intersects the threshold line.

The expression "threshold line" indicates the reference line chosen by the operator in order to intersect the curves in the exponential phase.

"Target" indicates that the target of the investigation and analysis is the frataxin, whose levels of mRNA are evaluated in the cell samples with or without ("control") diazoxide.

"Control" indicates the cell sample not treated with diazoxide.

According to this preferred embodiment of the invention, step (d') is performed by substituting the mathematical formula $2^{-\Delta\Delta Ct}$ with the values of the difference between the threshold cycle of the target in the samples treated and not treated (control) with diazoxide, normalized with the threshold cycle value of the reference gene (actin), in the case in question $$\Delta Ct = Ct\, Hs00175940\_m1 - Ct\, Hs99999903\_m1.$$

$$\Delta\Delta Ct = \Delta Ct(\text{treated sample}) - \Delta Ct(\text{control sample})$$

The results can be analysed by means of appropriate software, after setting the baseline and threshold cycle values.

The result of the calculation $2^{-\Delta\Delta Ct}$ represents the relative quantification value. Said value permits determination of the quantity of frataxin (which represents the target) in the sample treated with diazoxide with respect to the quantity of frataxin in the sample not treated with diazoxide (which represents the control) normalized for the quantity of actin (which represents the reference or internal standard) in said sample.

The present invention is better illustrated by means of the examples, given below, which in no way constitute a limitation.

Example 1

Process for Treating the Cell Lines In Vitro with diazoxide or 7-chloro-3-methyl-4H-1,2,4 benzothiadiazine 1,1-dioxide The human cell line HEK 293 (Human Embryonic Kidney) grown in Dulbecco's modified Eagle's medium (DMEM, Sigma) with the addition of 10% foetal bovine serum (FBS) (v/v), glutamine 2 mM, penicillin 100 unit/ml and streptomycin 100 μg/ml is kept in an incubator at a temperature of 37° C. and 5% $CO_2$.

Preferably the HEK 293 cells, cultured on 60 mm plates at a concentration of $0.5 \times 10^6$, after at least 14 hours of growth have a 70-80% confluence. Diazoxide is added to the culture medium of said cells at a concentration of 100 μM with glucose 20 mM and the cells are kept in an incubator for 24 hours at a temperature of 37° C. and 5% $CO_2$; the culture medium is not replaced during the incubation period.

Example 2

Extraction of Total RNA and Reverse-Transcription

Extraction of the RNA from the cells is performed according to the indications contained in the QIAconnect Gene Expression (Qiagen) kit. Particularly the samples are lysed and homogenated. Ethanol is then added to the treated samples to provide ideal conditions for the bond with the silica-gel RNase membrane. In this way the RNA binds and the contaminants are washed; the pure RNA is concentrated and eluted.

The concentration of the extracted RNA is determined by UV spectrophotometric method under suitable reading conditions. The reverse transcription reaction is performed with the GeneAmp RNA PCR core (Applied Biosystems) kit according to the indications provided by the manufacturer.

Example 3

Quantitative Real-Time RT-PCR

Quantification of the reverse-transcribed product is performed using fluorescent probes capable of hybridizing and specifically pairing DNA regions of interest. The probes used according to the invention are Probe Hs 00175940_m1 and Probe Hs 99999903 ml (Applied Biosystems). Particularly the probe defined Hs 00175940_m1 represents the specific probe able to recognise and hybridize the human frataxin gene, while the probe Hs 99999903 ml recognises the human actin and is useful for normalising the mRNA values of the target.

The analyzing step of the results is performed by substituting the mathematical formula $2^{-\Delta\Delta Ct}$ with the difference between the target threshold cycle in the samples treated and not treated (control) with diazoxide, normalised with the threshold cycle value of the reference gene (actin), in the case in question $$\Delta Ct = Ct\,Hs00175940\_m1 - Ct\,Hs99999903\_m1.$$

$$\Delta\Delta Ct = \Delta Ct(\text{treated sample}) - \Delta Ct(\text{control sample})$$

The results can be analysed by means of appropriate software, after setting the baseline and threshold cycle values.

The result of the calculation $2^{-\Delta\Delta Ct}$ represents the relative quantification value. Said value permits determination of the quantity of frataxin (which represents the target) in the sample treated with diazoxide with respect to the quantity of frataxin in the sample not treated with diazoxide (which represents the control) normalised for the quantity of actin (which represents the reference or internal standard) in the same sample.

For example a value of 1 is attributed to the control samples, i.e. HEK 293 cells not treated with diazoxide chosen as references.

As shown in FIG. 1, the cells treated with diazoxide 100 µM with glucose 20 mM have an increased quantity of frataxin with respect to the non-treated control and with respect to the same cells treated alternatively with diazoxide or glucose.

Example 4

Evaluation of the Effect of the Combination of Diazoxide and Glucose after 24 Hours The expression level and therefore the quantity of frataxin of cells deriving from HEK 293 cell lines, treated as described in examples 1, 2 and 3 was compared 24 hours after the treatment.

Figure 2:
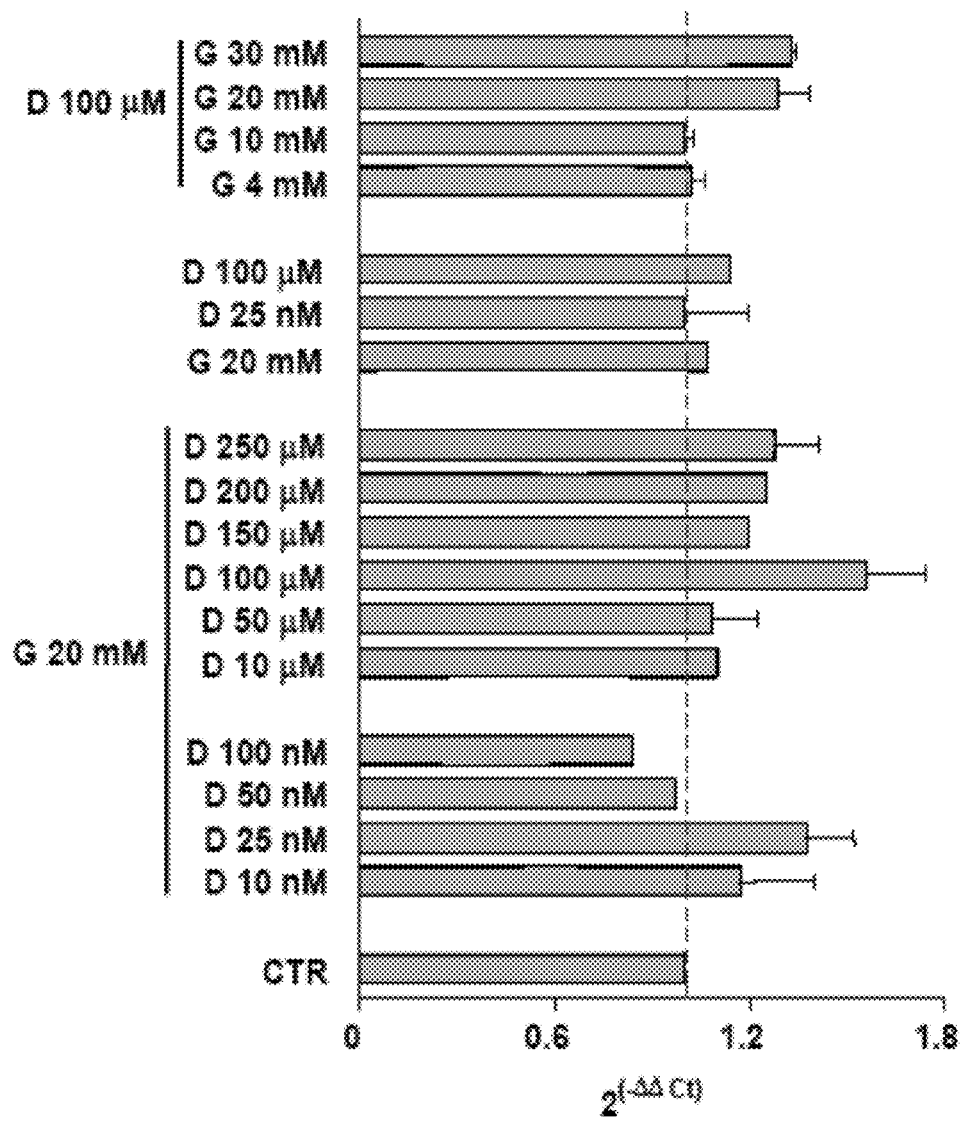
FIG. 2 is a histogram showing results from testing the diazoxide and the glucose at different concentrations and in different combinations with respect to a treated sample of cells. A broken vertical line represents the threshold value above which the increase in frataxin expression can be seen.

As shown in FIG. 2, the cells were treated testing the diazoxide and the glucose at different concentrations and in different combinations. Particularly the broken vertical line represents the threshold value above which the increase in frataxin expression can be seen. The experiment was conducted as follows, testing the cells with:
fixed concentration of diazoxide 100 µM and variable concentrations of glucose 4, 10, 20 and 30 mM;
fixed concentration of glucose 20 mM and concentrations of diazoxide varying between 10 nM and 250 µM;
fixed concentration of diazoxide 25 nM or 100 µM without glucose;
fixed concentration of glucose 20 mM without diazoxide.

The experiment demonstrates that the frataxin expression levels in the case of samples treated with diazoxide only or with glucose only show a minimum deviation from the threshold line, or coinciding with the non-treated control, whereas the optimal concentration to obtain a significant deviation from the threshold line, and therefore an increase in the frataxin expression, is a concentration of diazoxide 100 µM combined with a concentration of glucose 20 mM.

Example 5

Figure 3:
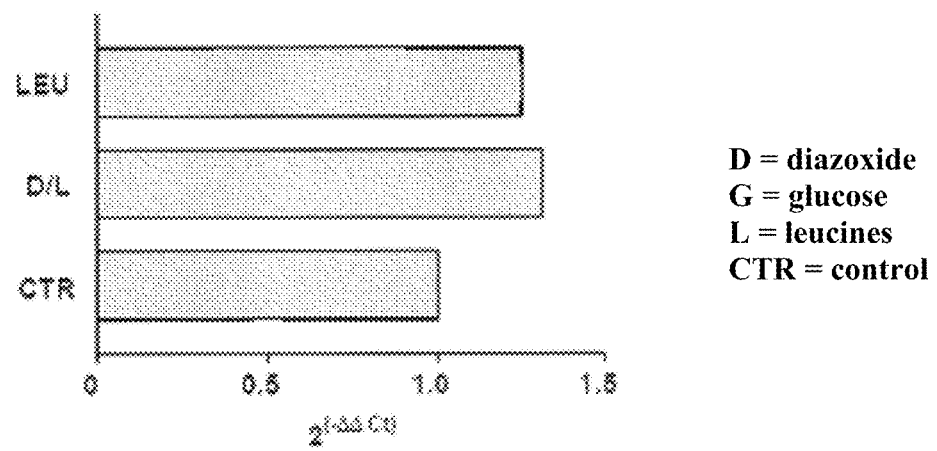
FIG. 3 is a histogram showing results from testing diazoxide and the leucine with respect to a non-treated control sample of cells.

Evaluation of the Effect of the Combination of Diazoxide and Leucine after 24 Hours The expression level and therefore the quantity of frataxin of cells deriving from HEK 293 cell lines, treated as described in examples 1, 2 and 3 was compared 24 hours after the treatment. The cells were treated testing the diazoxide and the leucine with respect to a non-treated control sample (FIG. 3).

The experiment demonstrates that the frataxin expression levels in the case of samples treated with leucine only at a concentration of 10 mM show a minimum deviation with respect to the non-treated control, whereas the optimal concentration of diazoxide 100 µM and leucine to obtain a significant deviation from the threshold line, and therefore increase in the frataxin expression, is a diazoxide concentration of 100 µM combined with a leucine concentration of 10 mM.

Example 6

Evaluation of the Effect of Diazoxide and Glucose

The expression level and therefore the quantity of frataxin of cells deriving from HEK 293 cell lines treated as described in examples 1, 2 and 3 was compared 24, 48 and 72 hours after treatment.

Figure 4:
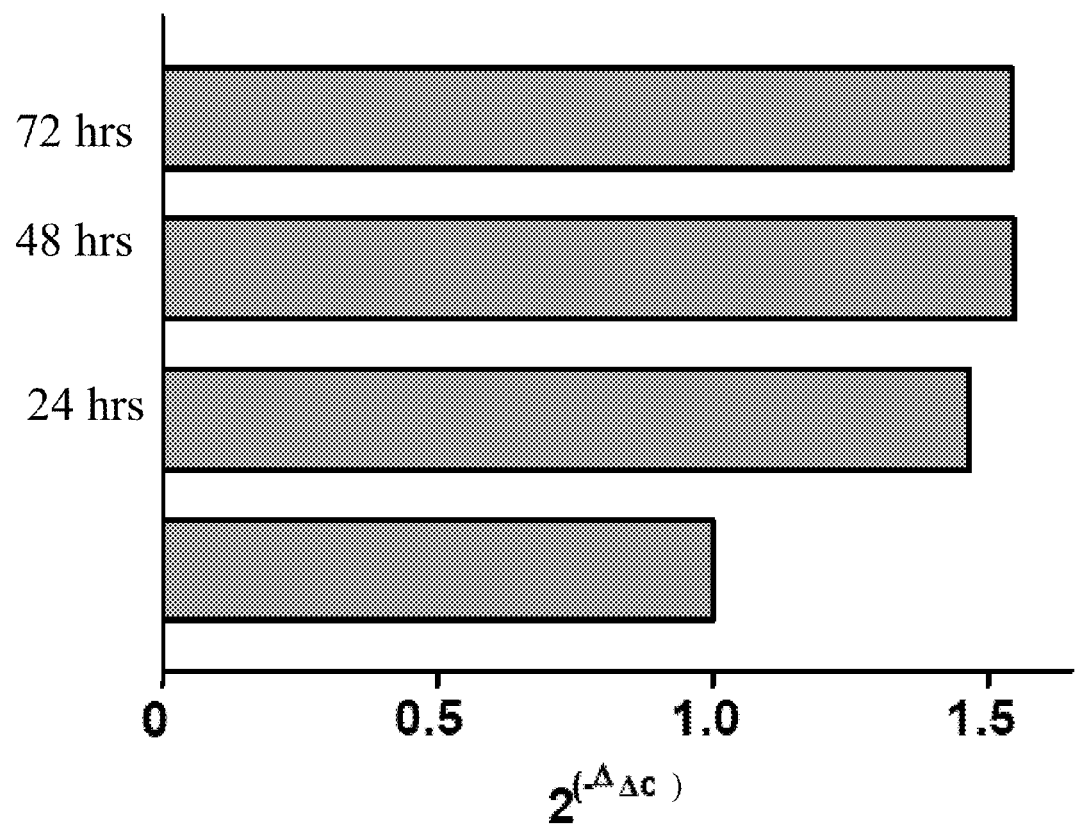
FIG. 4 is a histogram showing results from testing diazoxide 100 .mu.M together with glucose 20 mM with respect to a treated sample of cells. An increase in a quantity of frataxin with respect to the non-treated control remains constant even 48 and 72 hours after the treatment.

FIG. 4 shows that in the cells treated with diazoxide 100 µM together with glucose 20 mM, the increase in the quantity of frataxin with respect to the non-treated control remains constant even 48 and 72 hours after the treatment.

Example 7

Western Blot Analysis

The cells treated as described in example 1 are lysed with a lysis buffer (0.15 M NaCl, 5 mM EDTA, pH 8, 1% Triton X100, 10 mM Tris-Cl, pH 7.4) and transferred to microcentrifuge tubes. A quantity of approximately 50 µg of cell suspension is separated by electrophoresis in the presence of SDS (sodium dodecyl sulphate) at 17% (denaturing conditions). The resulting product is transferred onto nitrocellulose membranes. Identification of the presence of the target protein, i.e. the frataxin, is performed with a rabbit polyclonal primary antibody directed against said protein (Santa Cruz Biotechnology), and a goat-anti rabbit HRP secondary antibody (Pierce). The reaction was identified with enzymatic method by means of ECL plus system (Amersham).

Figure 5:
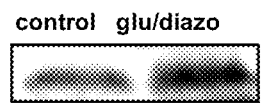
FIG. 5 is a western blot analysis that compares band intensity of frataxin quantity in treated cells and in control cells.

FIG. 5, reported below, shows that the frataxin quantity in the treated cells is greater than that of the control cells, as can be easily seen from comparison of the band intensity.

Figure 6:
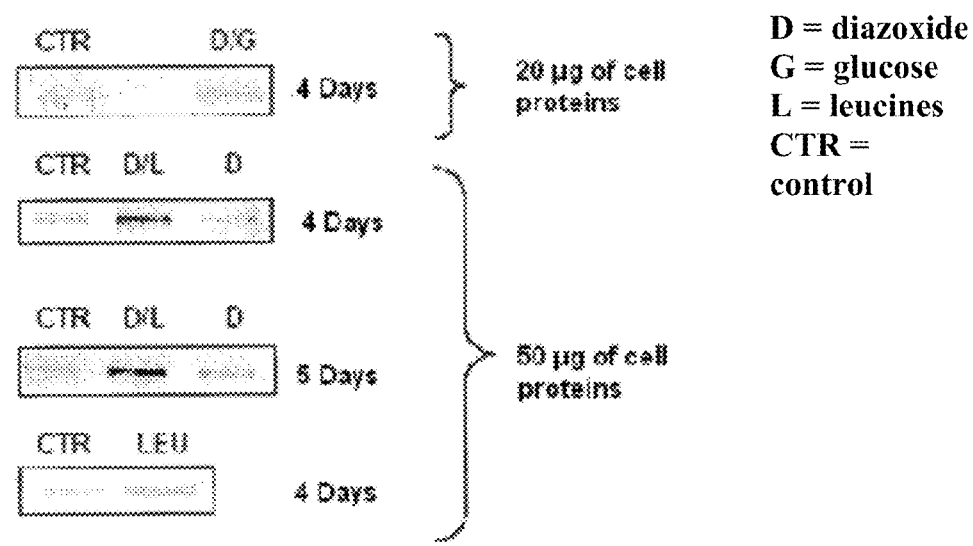
FIG. 6 is a western blot analysis that shows that the cells treated with diazoxide in combination with glucose or leucine maintain the increase in expression even 4 or 5 days after the initial treatment.

FIG. 6 shows that the cells treated with diazoxide in combination with glucose or leucine maintain the increase in expression even 4 or 5 days after the initial treatment. The results are even more surprising and significant if compared with the three internal controls, i.e. non-treated cells, cells treated with diazoxide only and cells treated with leucine only.

Figure 7:
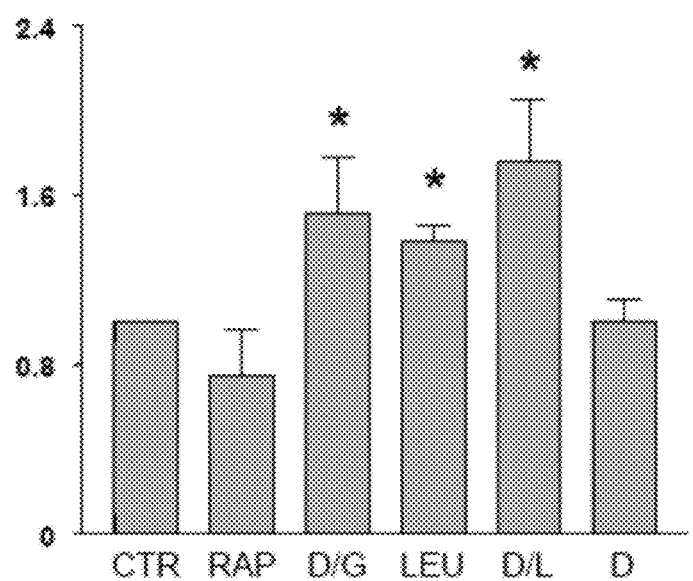
FIG. 7 is a histogram showing results from treatment combining the diazoxide with glucose or leucine.

In order to highlight the effectiveness of the treatment combining the diazoxide with glucose or leucine, the results were processed as a histogram (FIG. 7). The histograms indicated by the asterisk represent the samples on which the Student t—test was performed; the difference is significant for $p<0.05$.

Example 8

Evaluation of the Effect of the Combination of Diazoxide and Glucose after 24 Hours on Cells of Patients Affected The expression level and therefore the quantity of frataxin of cells deriving from immortalized lymphoblastoid cell lines of FRDA patients treated as described in examples 2 and 3 was compared 24 hours after the treatment.

Figure 8:
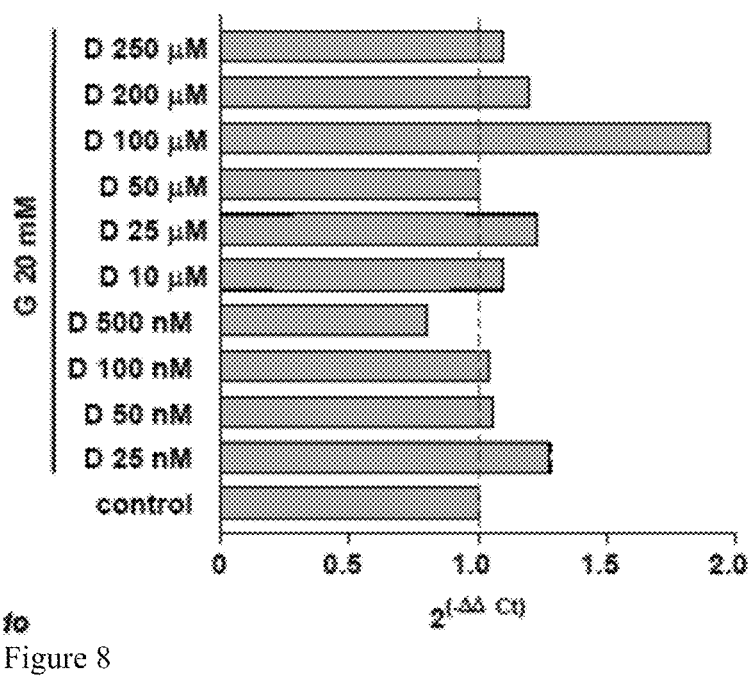
FIG. 8 is a histogram showing results of testing treated cells with diazoxide at different concentrations in combination with a fixed concentration of glucose. A broken vertical line represents the threshold value above which the increase in frataxin expression can be seen.

The histogram (FIG. 8) shows the treated cells testing with the diazoxide at different concentrations in combination with a fixed concentration of glucose. In particular, the broken vertical line represents the threshold value above which the increase in frataxin expression can be seen. The experiment was conducted testing the cells with concentrations of diazoxide varying from 25 nM to 100 µM in combination with fixed concentrations of glucose 20 mM.

The experiment demonstrates that the frataxin expression levels in the case of samples treated with diazoxide at various concentrations and in combination with glucose show a minimum deviation from the threshold line for some particular concentrations of diazoxide, while the optimal concentration to obtain a significant deviation from the threshold line, and therefore an increase in frataxin expression, is diazoxide 100 µM combined with glucose 20 mM.

Example 9

Evaluation of the Effect of the Combination of Diazoxide and Glucose or Diazoxide and Leucine after 24 Hours on Cells of Patients Affected by FRDA The expression and therefore the quantity of frataxin in cells deriving from immortalized lymphoblastoid cell lines of FRDA patients was compared.

Figure 9:
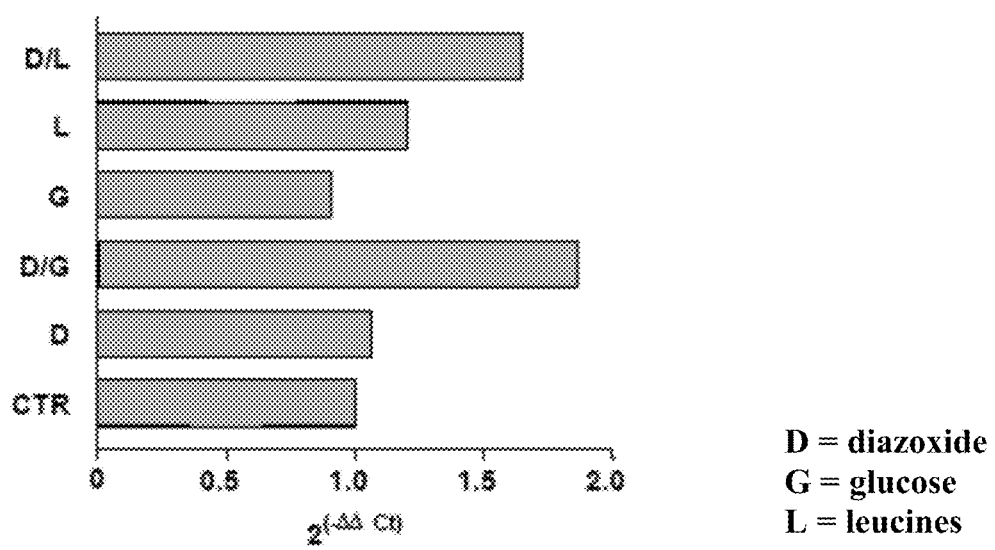
FIG. 9 is s histogram showing a synergic effect of the diazoxide used in combination with glucose or leucine.

FIG. 9 demonstrates and provides further proof of the synergic effect of the diazoxide used in combination with glucose or leucine.

Example 10

Western Blot Analysis

Figure 10:
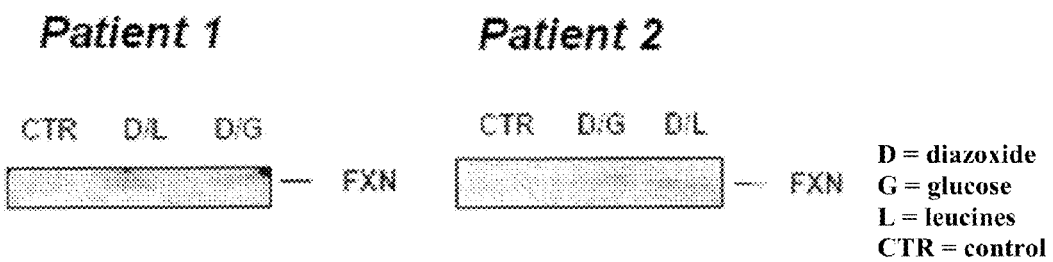
FIG. 10 is a western blot analysis that shows that the cells treated with diazoxide in combination with glucose or leucine maintain the increase in expression even 24 hours after the initial treatment. Cells of the patients treated according to the invention present an evident band as expression of the quantity of frataxin present with respect to the non-treated control.

FIG. 10 shows that the cells treated with diazoxide in combination with glucose or leucine maintain the increase in expression even 24 hours after the initial treatment. It can be seen that the cells of the patients treated according to the invention present an evident band as expression of the quantity of frataxin present with respect to the non-treated control.

Figure 11:
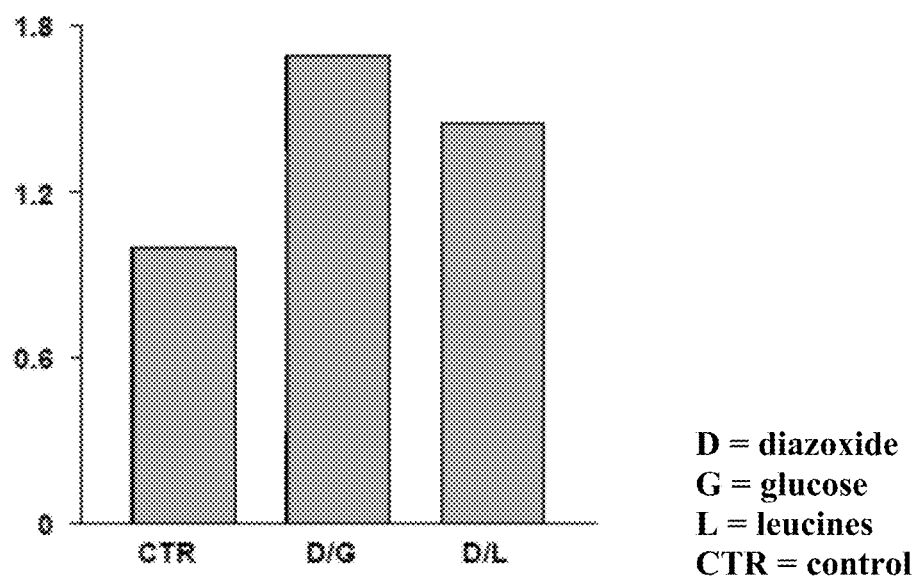
FIG. 11 is a histogram showing results of an experiment in which an increase in expression of the treated cells with respect to untreated control cells can be clearly seen.

The results of the experiment were processed also in the form of a histogram (FIG. 11), shown below, where the increase in expression of the treated cells with respect to the control can be clearly seen.

The present invention may be in the form of a kit that contains in a common package all components necessary for the determination of the levels of frataxin in an isolated biological sample, involving the use of diazoxide or 7-chloro-3-methyl-4H-1,2,4 benzothiadiazine 1,1-dioxide, in combination with glucose or leucine or both.

What is claimed is:

1. A pharmaceutical preparation, comprising 100 µM 7-chloro-3-methyl-4H-1,2,4 benzothiadiazine 1,1-dioxide, in combination with 20 mM glucose or both 20 mM glucose and 10 mM leucine, effective for treatment of Friedreich's ataxia.

2. The pharmaceutical preparation of claim 1, formulated as a tablet, capsule, or injectable solution.

3. A kit, comprising a common package containing components needed to effect determination of levels of frataxin in an isolated biological sample, comprising 100 µM 7-chloro-3-methyl-4H-1,2,4 benzothiadiazine 1,1-dioxide, in combination with 20 mM glucose or both 20 mM glucose and 10 mM leucine.

4. A pharmaceutical preparation, comprising 100 µM 7-chloro-3-methyl-4H-1,2,4 benzothiadiazine 1,1-dioxide, in combination with 10 mM leucine, for treatment of Friedreich's ataxia.

5. The pharmaceutical preparation of claim 4, formulated as a tablet, capsule, or injectable solution.

6. A kit, comprising a common package containing components needed to effect determination of levels of frataxin in an isolated biological sample, comprising 100 µM 7-chloro-3-methyl-4H-1,2,4 benzothiadiazine 1,1-dioxide, in combination with 10 mM leucine.

* * * * *